US012751659B2

(12) United States Patent
Gliner et al.

(10) Patent No.: US 12,751,659 B2
(45) Date of Patent: Oct. 6, 2026

(54) METHOD AND SYSTEM FOR IDENTIFYING DISCONNECTED CATHETER ELECTRODE

(71) Applicant: BIOSENSE WEBSTER (ISRAEL) LTD., Yokneam (IL)

(72) Inventors: Vadim Gliner, Haifa (IL); Assaf Govari, Haifa (IL); Uri Avni, Ram-On (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 550 days.

(21) Appl. No.: 18/369,960

(22) Filed: Sep. 19, 2023

(65) Prior Publication Data

US 2025/0090068 A1 Mar. 20, 2025

(51) Int. Cl.

*A61B 18/14* (2006.01)
*A61B 5/287* (2021.01)
*A61B 18/24* (2006.01)

(52) U.S. Cl.

CPC ........ *A61B 5/287* (2021.01); *A61B 2562/226* (2013.01)

(58) Field of Classification Search

CPC ...... A61B 18/1492; A61B 2018/00214; A61B 2018/00351; A61B 2018/0022; A61B 2018/0016; A61B 2018/1467; A61B 2018/00839; A61B 2018/00267; A61B 2018/126; A61B 18/14; A61B 2018/00642; A61B 2017/00243; A61B 2090/065; A61B 18/24; A61B 5/6852; A61B 2018/00666;

(Continued)

(56) References Cited

U.S. PATENT DOCUMENTS 5,391,199 A 2/1995 Ben Haim
5,443,489 A 8/1995 Ben Haim (Continued)

FOREIGN PATENT DOCUMENTS

EP 4029449 A1 7/2022

OTHER PUBLICATIONS

Earley et al. "Validation of the Noncontact Mapping System in the Left Atrium During Permanent Atrial Fibrillation and Sinus Rhythm" Journal of the American College of Cardiology. vol. 48, No. 3, 2006 (Year: 2006).*

(Continued)

*Primary Examiner* — Joseph A Stoklosa
*Assistant Examiner* — Brian M Antiskay

(57) ABSTRACT

A method, apparatus and computer program product, the method comprising: obtaining a plurality of electrical signals obtained from a plurality of electrodes distally disposed on a catheter inserted into one or more chambers of a heart of a patient, wherein one or more electrical signals obtained from one or more electrodes of the plurality of electrodes obtains electrical activity in one or more locations within the heart; identifying one or more signals from the plurality of electrical signals as being emitted from one or more disconnected electrode, said identifying utilizing a correlation with a reference signal measured within the heart, wherein the reference signal is associated with a reference electrode; and generating a map of electrical activity within the heart based upon the plurality of electrical signals, excluding one or more electrical signals originating from the disconnected electrodes.

11 Claims, 4 Drawing Sheets

(58) Field of Classification Search
CPC ......... A61B 5/053; A61B 5/24; A61B 5/1473; A61B 5/282; A61N 1/05; A61N 1/04; A61M 25/10
USPC ............. 600/372–381, 508–509; 606/20–42; 607/118–123
See application file for complete search history.

(56) References Cited

U.S. PATENT DOCUMENTS

| | | | |
|---|---|---|---|
| 5,558,091 A | | 9/1996 | Acker |
| 6,172,499 B1 | | 1/2001 | Ashe |
| 6,239,724 B1 | | 5/2001 | Doron |
| 6,332,089 B1 | | 12/2001 | Acker |
| 6,484,118 B1 | | 11/2002 | Govari |
| 6,618,612 B1 | | 9/2003 | Acker |
| 6,690,963 B2 | | 2/2004 | Ben Haim |
| 6,788,967 B2 | | 9/2004 | Ben Haim |
| 6,892,091 B1 | | 5/2005 | Ben Haim |
| 7,536,218 B2 | | 5/2009 | Govari |
| 7,756,576 B2 | | 7/2010 | Levin |
| 7,848,787 B2 | | 12/2010 | Osadchy |
| 7,869,865 B2 | | 1/2011 | Govari |
| 8,456,182 B2 | | 6/2013 | Bar-Tal |
| 8,676,305 B2 | | 3/2014 | Hayam et al. |
| 9,629,567 B2 | | 4/2017 | Porath et al. |
| 11,660,050 B2 | * | 5/2023 | Govari ................. A61B 5/6853 600/374 |
| 2016/0331267 A1 | | 11/2016 | Maskara et al. |
| 2023/0052130 A1 | | 2/2023 | Govari et al. |
| 2023/0112251 A1 | | 4/2023 | Govari et al. |

OTHER PUBLICATIONS

Extended European Search Report, received for European Application No. 24200962.9, mailed on Feb. 25, 2025, 08 pages.

* cited by examiner

METHOD AND SYSTEM FOR IDENTIFYING DISCONNECTED CATHETER ELECTRODE

FIELD OF THE DISCLOSURE

This disclosure relates generally to a method for identifying disconnected electrodes during a cardiac diagnostic operation, and to using the information about electrodes identified as disconnected.

BACKGROUND OF THE DISCLOSURE

Arrhythmias may be caused by problems with the electrical conduction system of the heart, and in particular electrical activity in one or more points or areas on a wall of a heart chamber. Atrial fibrillation is an arrhythmia characterized by disorganized signals that make the atria (left and/or right atria) squeeze very fast and in an asynchronous cardiac rhythm.

In order to assess the status of the patient and decide on the treatment, such as applying one or more ablations, it may be required to assess the electrical activity at multiple locations of the heart wall. This activity may be obtained from a plurality of electrodes positioned on a distal tip of an intracardiac catheter inserted into one or more chambers of the heart. A plurality of the obtained signals may be displayed to a user, such as a physician performing the operation. The obtained signals may also be used for generating a map of the electrical activity within the heart.

BRIEF DESCRIPTION OF THE DRAWINGS

The present disclosure will be more fully understood from the following detailed description of the examples thereof, taken together with the drawings, in which.

DETAILED DESCRIPTION OF EXAMPLES

Figure 1:
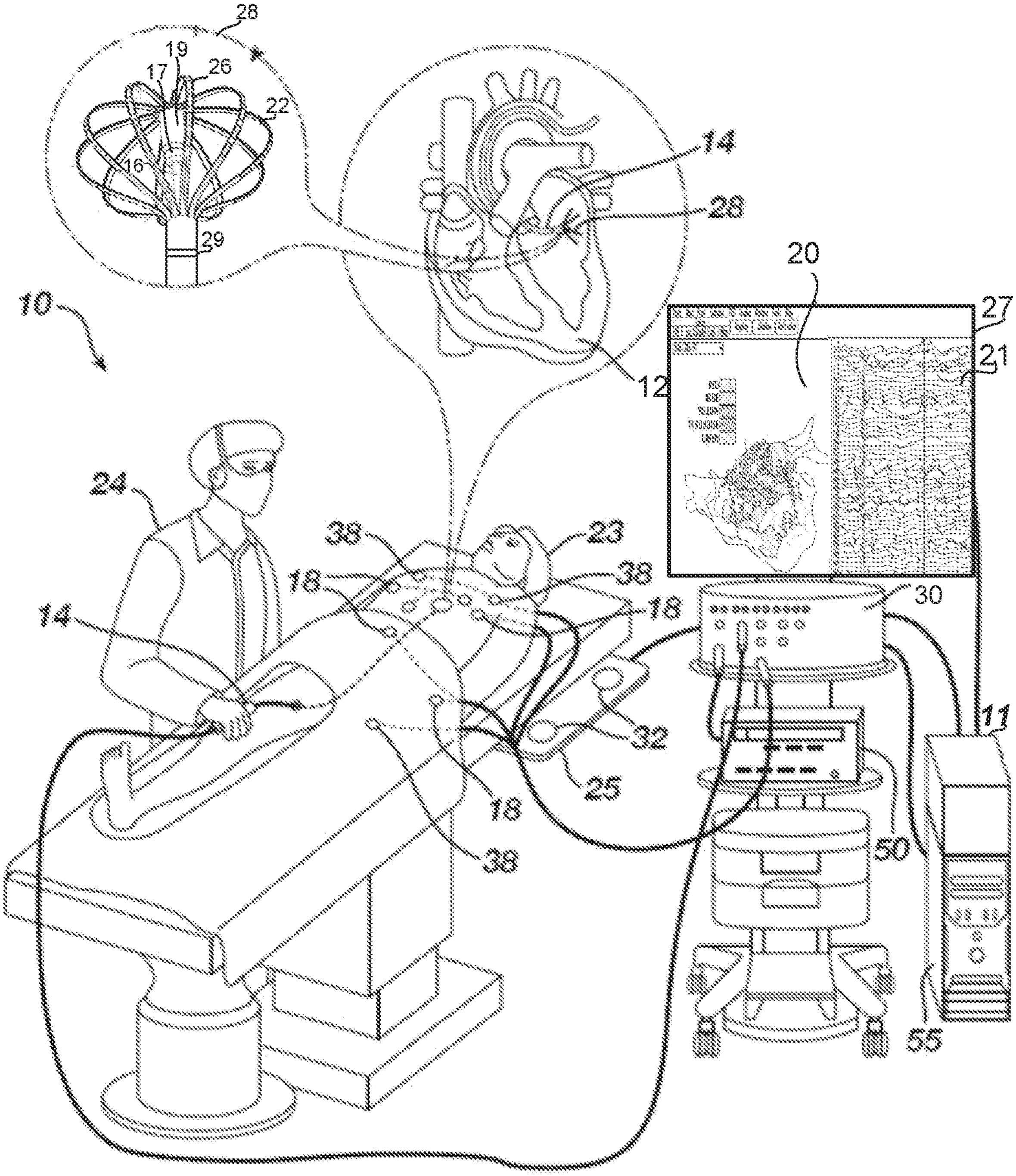
FIG. 1 is a schematic, pictorial illustration of a catheter-based electrophysiological (EP) mapping and ablation system.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Overview

Arrhythmogenic tissue related to atrial fibrillation may be identified by inspecting Intracardiac Electrogram (IEGM) at one or more locations over an atria wall, e.g., inner wall, to detect the local potential caused by depolarization in each of the one or more locations.

The IEGM is typically detected with one or more electrodes on a distal tip of an intracardiac catheter. In some example embodiments, the intracardiac catheter additionally includes a position sensor configured to track position of the distal tip.

Modern catheters have a plurality of electrodes distributed over a plurality of splines of the catheter, Where at any given time, each electrode samples the electrical activity at a location. For example, some catheters may have dozens or even a hundred electrodes. It is appreciated that the plurality of electrodes enables the collection of significant amounts of data and can give a good overall view of the electrical activity within the heart.

Typically, the signal output by each electrode comprises the actual signal of the electrical activity, as well as noise produced in the environment, such as the far field signal which represents the noise in the blood pool within the heart chamber. Typically, the magnitude of far-field signal is expected to be significantly greater than that of actual signal of the electrical activity. The actual signal is measured as the potential difference between the electrode and a reference which does not touch the heart wall and thus captures only the far field signal. The reference may be a reference electrode in the blood pool or Wilson Central Terminal (WCT). The potential difference is thus a signal indicating the heart activity at the location of the electrode.

A problem that may occur with a multi-electrode catheter is a physical disconnection of one or more electrodes, when a wire connecting an electrode to the Patient Interface Unit (PIU) disconnects from the electrode or breaks somewhere along a channel running along a shaft of the catheter. Output provided by a disconnected electrode, which, as detailed above, is measured relative to the reference electrode is dominated by the reference signal multiplied by minus 1.

Incorporating these non-representative signals into the electrical map of the heart harms the integrity of such map, which may lead to wrong decisions. Moreover, if too many of the electrodes are disconnected, the heart map as a whole and hence the operation may prove irrelevant and lead to dangerous decisions.

Furthermore, displaying to the user electrograms of the irrelevant signals in addition to the other signals provides to the users incorrect information, and also clutters the display, thus disturbing the user from inspecting the correct and relevant information.

Therefore, the challenge is to identify these electrodes, such that the signals associated with them may be ignored and not used in calculating the electrical activity map of the heart, not displayed to the user such as the physician, nor used in any other way.

Known techniques for detecting disconnected electrodes require the injection of additional signals dedicated for this purpose to the patient's heart, which is undesired. For example, some techniques include driving current between two electrodes, such that potential difference is generated. If one of the electrodes is disconnected, the resistance and thus the potential difference approaches infinity, thus providing for discovering the disconnected electrode. However, this technique requires the driving of significant currents into the body which is undesired.

The electrical activity captured by the electrodes may be inspected in the form of a unipolar signal (U1, U2, U3, . . . ) and/or in the form of a bipolar signals (B1, B2, B3 . . . ). Unipolar signals represent the potential difference between the outputs from an electrode and a reference as described herein above. Bipolar signals represent a potential difference between a pair of electrodes that are configured to sense the electrical activity of the heart. Bipolar signals are a unipolar signal from one electrode (of a pair of sensing electrodes) subtracted by a unipolar signal from another electrode (of the pair of sensing electrodes). For example, B1 may represent the difference between unipolar signals on electrodes 1 and 2, e.g., U2-U1.

When unipolar signals are used for obtaining output from each electrode, wherein the electrode signal comprising the heart activity and the far field signal is measured relative to the reference signal as measured by the reference electrode, thus outputting the heart activity at the electrode location.

If the wire is disconnected from the electrode, the electrode signal as measured relative to the reference electrode will be dominated by the reference signal multiplied by minus one.

Correlating this alleged heart activity signal with the reference signal, will provide output which is substantially close to −1, for example within the range of [(−1.1) . . . (−0.9)], [(−1.05) . . . (−0.95)], or the like.

Therefore, by correlating the output of each electrode with the signal of the reference electrode which is known not to touch the heart wall, a disconnected electrode may be identified.

If the bipolar methodology is used, assume that U1, U2 and U3 are the signals representing the heart activity at locations of three electrodes that are close to one another, for example are consecutive electrodes located on the same spline of the catheter. B1 denotes the potential difference between U1 and U2, and B2 denotes the potential difference between U2 and U3.

Thus, B1=U1−U2 and B2=U2−U3, wherein each U signal is measured as above relative to the reference signal.

If the electrode associated with U2 is disconnected, its measured signal (is as above dominated by (−reference_signal), such that B1 and B2 are as follows: B1=U1−U2=U1−(−reference signal)=~U1+reference signal B2=U2−U3=−reference signal−U3=~−U3−reference signal Since U1 and U3 are significantly lower than the reference signal, correlating B1 which is substantially the same as the reference signal and B2 which is substantially the same as (−reference signal), will yield approximately (−1), as above.

Thus, examining the bipolar signals of three consecutive electrodes may provide for identifying whether the middle electrode of the three is disconnected.

The disclosure thus provides for identifying disconnected electrodes using Electrocardiography (ECG) signals, rather than by applying additional signals for identifying disconnected electrodes based on resistance changes. Since the total extent of electrical signals provided to the heart is limited, using the available ECG signals is advantageous as it eliminates the need to add surplus signals.

It is appreciated that if the reference signal is unavailable, a Wilson Central Terminal (WCT) signal, which averages the signals captured over the user's body may be used instead.

The identification of one or more electrodes as disconnected may be used in a plurality of ways.

In some embodiments, the signals associated with disconnected electrodes may be left out when generating the electrical map of the heart, such that incorrect information does not affect the results. Moreover, the number or percentage of the disconnected electrodes out of all electrodes may be calculated, and if exceeds a certain threshold, the operation may be discontinued since the results do not provide a sufficient picture of the heart's electrical activity.

In some embodiments, eliminating the display of irrelevant and incorrect electrograms, such as those associated with disconnected electrodes provides for displaying only true and relevant information, and reduces the display cluttering, thus making it easier for the user to inspect the true information.

In some embodiments, the electrodes identified as disconnected may be reported to a user or another person, such as a physician, a technician, or the like.

System Description

Reference is made to FIG. 1 showing an example catheter-based electrophysiology mapping and ablation system 10. System 10 includes multiple catheters, which may be percutaneously inserted by a physician 24 through the vascular system of a patient 23 into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician 24 may place electrode assembly 28 of catheter 14 in contact with the heart wall for sensing a target site in heart 12. For ablation, physician 24 may similarly place a distal end of an ablation catheter in contact with a target site for ablating tissue.

Catheter 14 is an exemplary catheter that is basket-shaped and includes one and preferably multiple electrodes 26 optionally distributed over a plurality of splines 22 at electrode assembly 28 and configured to sense the IEGM signals. Each electrode 26 is connected via a wire (not shown) going through or attached to spline 22 towards Patient interface unit (PIU) 30 detailed below. Splines 22 may be directly or indirectly attached to a central longitudinal axis of electrode assembly 28. The longitudinal axis may have coupled thereto electrode 17. By design, even when electrode assembly 28 is within a chamber of the heart, and one or more electrodes 26 is in contact with the heart wall, electrode 17 is in a position internal to the heart chamber and cannot make contact with the heart wall.

Therefore, electrode 17 measures the far field signal, representing the noise within the blood pool.

Catheter 14 may additionally include a position sensor 29 embedded in or near electrode assembly 28 for tracking position and orientation of electrode assembly 28. Optionally and preferably, position sensor 29 is a magnetic based position sensor including three magnetic coils for sensing three-dimensional (3D) position and orientation. Electrode assembly 28 is further detailed in association with FIG. 2 below.

Magnetic based position sensor 29 may be operated together with a location pad 25 including a plurality of magnetic coils 32 configured to generate magnetic fields in a predefined working volume. The real time position of electrode assembly 28 of catheter 14 may be tracked based on magnetic fields generated with location pad 25 and sensed by magnetic based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

Additionally or alternatively, system 10 may include one or more electrode patches 38 positioned for skin contact on patient 23 to establish location reference for location pad 25 as well as impedance-based tracking of electrodes 26. For impedance-based tracking, electrical current is directed to electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

System 10 displays over display device 27 a plurality of electrograms 21 captured by electrodes 26 of catheter 14 and/or body surface ECG electrodes 18. Recorder 11 may include pacing capability for pacing the heart rhythm and/or may be electrically connected to a standalone pacer.

PIU 30 may be configured to establish electrical communication between catheters, other electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software stored therein, and user interface capability. Workstation 55 may provide multiple functions, optionally including (1) modeling the endocardial anatomy in three-dimensions (3D) based upon the signals received from electrodes 26 and rendering the model or anatomical map 20 for display on a display device 27; (2) displaying on display device 27 activation sequences (or other data) compiled from recorded electrograms 21 in representative visual indicia or imagery superimposed on the rendered anatomical map 20; and (3) displaying real-time location and orientation of multiple catheters within the heart chamber. One commercial product embodying elements of system 10 is available as the CARTO™ 3 System, available from Biosense Webster, Inc., 31A Technology Drive, Irvine, CA 92618.

As can be seen, a large number of electrograms 21 may be displayed, which may include one or more electrograms associated with disconnected electrodes, therefore these electrograms are incorrect and irrelevant.

Figure 2:
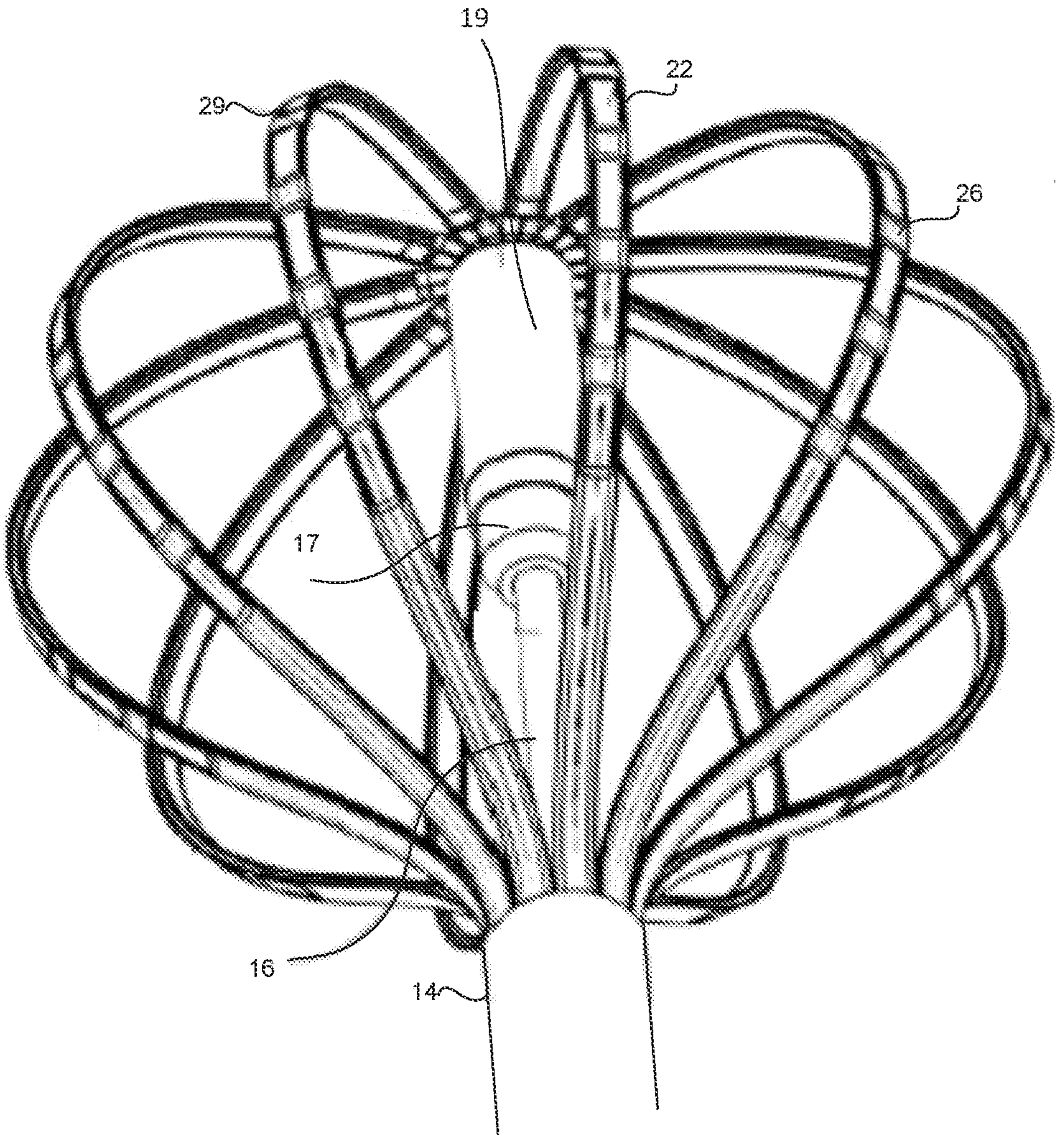
FIG. 2 shows a detailed view of a basket-shape catheter tip which can be used in accordance with some exemplary embodiments of the disclosure.

Reference is made to FIG. 2, showing a more detailed view of the basket-shaped electrode assembly 28 of FIG. 1. An example of a basket-type catheter is CLARYSENSE™ catheter, available from Biosense Webster, Inc., 31A Technology Drive, Irvine, CA 92618.

Electrode assembly 28 may be mounted on a distal end of catheter 14. Electrode assembly 28 may comprise electrode-carrying splines 22 which may be made of flexible polymer circuit strips, each carrying a plurality of electrodes 26, e.g., 10 arms carrying ten electrodes 26 each, providing a total of 100 electrodes. In other embodiments, electrode assembly 28 may carry between about five and about ten splines, for example about eight splines. In some embodiments, electrodes 26 may not be disposed, or may be disposed more sparsely, on the proximal portions of splines 22.

Splines 22 may be attached to the center longitudinal axis of electrode assembly 28, for example splines 22 may be connected to connector 19 disposed along the axis. Splines 22 may be generally evenly-spaced around the axis. Splines 22 may be actuated by a relative longitudinal movement of their ends along the axis. The axis may comprise a pusher 16, such that pusher 16 pushes into connector 19. When pusher 16 is pushed distally into connector 19, splines 22 curve. While electrode assembly 28 is within a heart chamber, the curving causes electrodes 26 to spread within the heart chamber, such that at least some of the electrodes may make contact with the chamber wall and sense the IEGM signals, while other electrodes 26 may assume a position internal to the heart chamber.

As mentioned above, the structure of electrode assembly 28 ensures that splines 22 surround the central axis and in particular electrode 17 mounted on the central axis, such that electrode 17 cannot touch the heart wall and its output comprises only the far field signal present in the blood pool, also referred to as reference signal.

Figure 3:
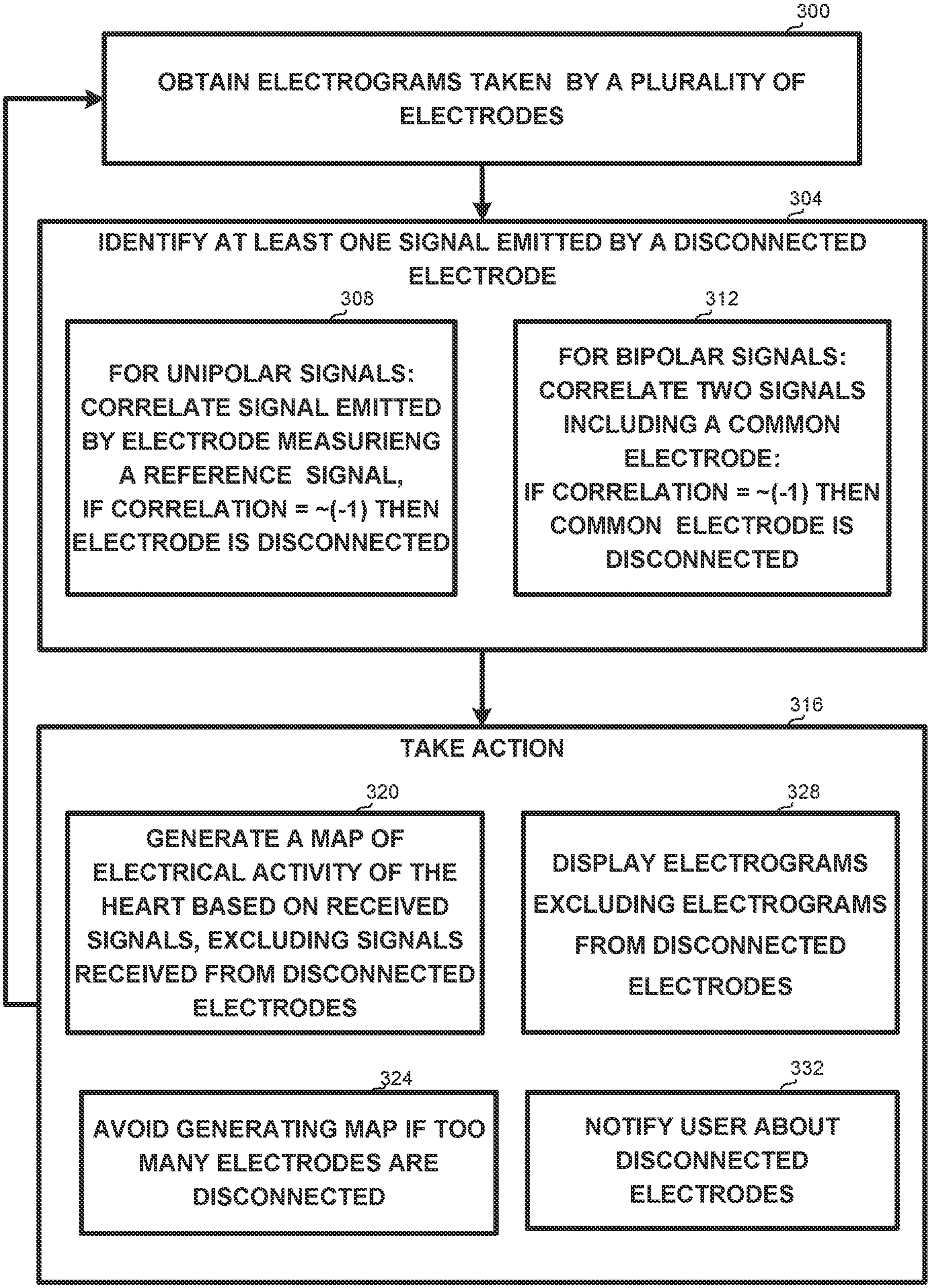
FIG. 3 is a flowchart of steps in a method for identifying disconnected electrodes and using information about the disconnected electrodes, in accordance with some exemplary embodiments of the disclosure.

Reference is now made to FIG. 3, showing a flowchart of steps in a method for identifying disconnected electrodes and using information about the disconnected electrodes, in accordance with some exemplary embodiments of the disclosure.

At step 300, electrograms are obtained which are taken by a plurality of electrodes distally disposed on a catheter inserted into one or more chambers of a heart of a patient. Each of at least some of the electrodes obtains electrograms at one or more locations within the one or more chambers.

At step 304, the electrograms may be examined to identify at least one electrode which is disconnected, i.e., its wire is disconnected from the electrode or is broken somewhere along the channel.

Step 304 may be performed by applying the unipolar technique and/or the bipolar technique for obtaining the signals associated with the electrodes.

Step 308 may be applied when using the unipolar technique for obtaining the electrode signal.

Using this technique, the measured signal is comprised of the actual signal and the noise signal. Thus, the actual signal may be estimated as the measured signal minus the noise signal, the noise signal provided by the reference electrode, such as electrode 17. If the tested electrode is disconnected, the measured signal will be close to zero, and thus the actual signal will be close to minus the reference signal. Therefore, if the correlation between the reference signal and the actual signal is close to −1, for example deviates in up to a predetermined threshold from −1, it may be assumed that the relevant electrode is disconnected.

Step 312 may be applied when using the unipolar technique for obtaining the electrode signal.

In the bipolar technique, a potential difference is measured between two consecutive or otherwise nearby electrodes, for example electrodes located on the same spline.

Using this technique, the potential differences between two pairs of electrodes having one electrode in common may be obtained, for example B1=U1−U2 and B2=U2−U3, wherein U1, U2 and U3 are signals indicating the difference between the heart activities at the locations of the two electrodes.

If the electrode associated with $U_2$ is disconnected, $B_1$ and $B_2$ will be as shown by the following formulas:

$$B_1 = U_1 - U_2 = U_1 - (\sim 0 - \text{reference\_signal}) = \sim U_1 + \text{reference\_signal}$$

$$B_2 = U_2 - U_3 = (\sim 0 - \text{reference\_signal} - U_3 = \sim(-U_3 - \text{reference\_signal})$$

Since each of $U_1$ and $U_3$ are significantly lower in magnitude than the reference signal, correlating $B_1$ which is substantially the same as the reference signal with $B_2$ which is substantially the same as (−reference_signal), will yield approximately −1, e.g., deviate at most by a predetermined threshold from −1.

It is appreciated that the extreme electrodes on each spline cannot be checked using the bipolar technique.

The computation may be repeated for all electrodes. For example, the computation may be repeated every predetermined period of time, only when the catheter is within the heart, according to a user's command, or according to any other condition or protocol. In some embodiments, repeating the process may be omitted for electrodes that have already been detected as disconnected on a previous check.

At step 316, once disconnected electrodes have been identified, one or more actions may be taken.

For example, at step 320, a map of the electrical activity of the heart may be generated based on the signals obtained from all electrodes, excluding the signals associated with electrodes identified as disconnected.

Moreover, at step 324, the ratio between the disconnected electrodes and all electrodes may be calculated. If the ratio or the number of disconnected electrodes exceeds a predetermined threshold, the map generation may be avoided, since the collected data is insufficient to provide a reliable map.

In another example, at step 328, electrograms of the signals obtained from all electrodes may be displayed, excluding the electrodes identified as disconnected.

In yet another example, at step 332, a user such as a physician, a technician or the like may be notified of the disconnected electrodes. Notification may take the form of sending a message, updating a database, displaying a warning on a display device, or the like.

Figure 4:
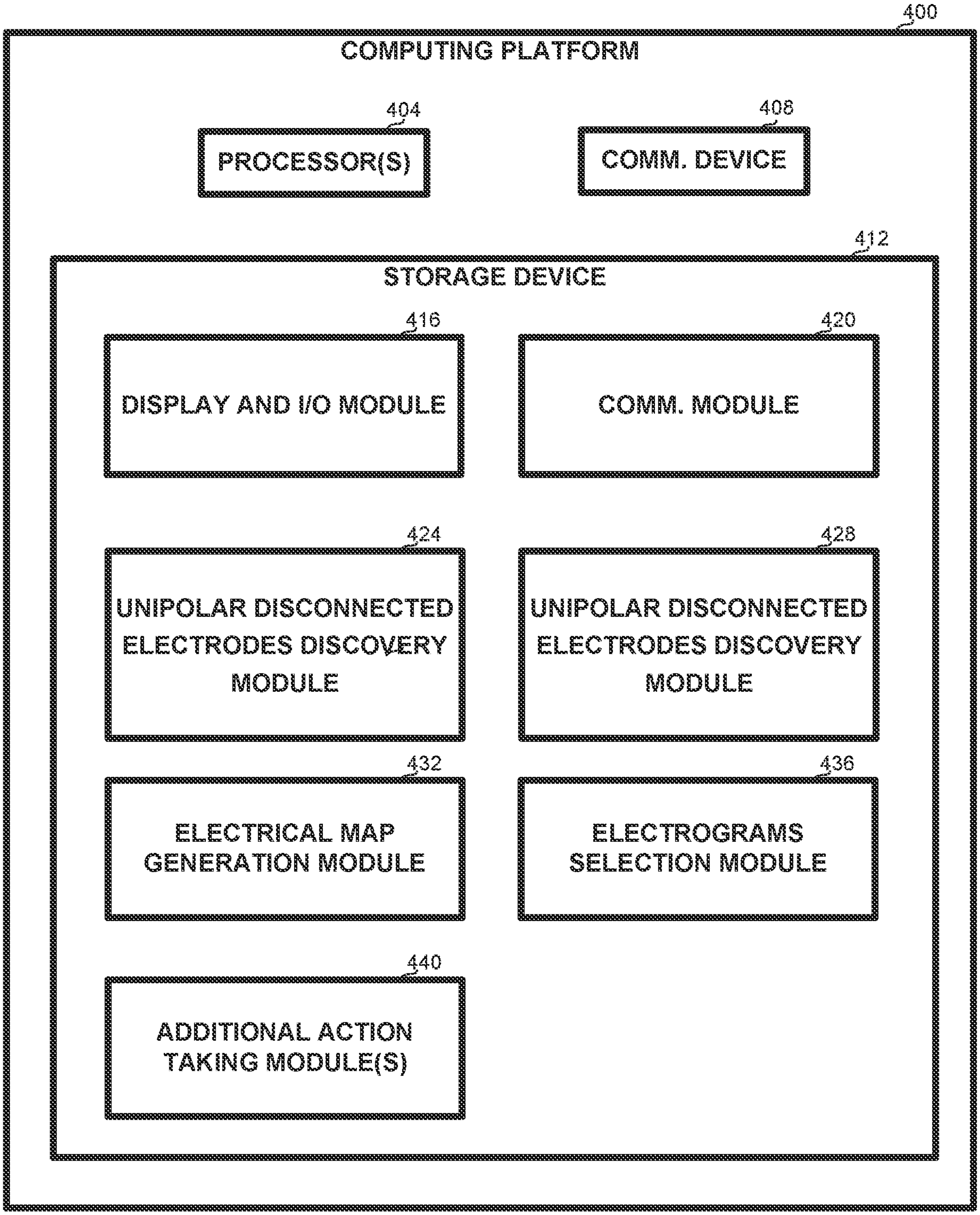
FIG. 4 is a schematic block diagram of a computing platform for identifying disconnected electrodes and using information about the disconnected electrodes, in accordance with some exemplary embodiments of the disclosure.

Referring now to FIG. 4, showing a block diagram of a computing platform 400 for detecting disconnected electrodes and using information about these electrodes, in accordance with some exemplary embodiments of the disclosure.

It is appreciated that computing platform 400 may be embedded within workstation 55, but may also be a standalone computing platform or embedded elsewhere and be in operative communication with workstation 55.

Computing platform 400 may be implemented as one or more computing platforms which may be operatively connected to each other. For example, one or more remote computing platforms, which may be implemented for example on a cloud computer. Other computing platforms may be a part of a computer network of the associated organization. In other embodiments, all the functionality may be provided by one or more computing platforms all being a part of the organization network.

Computing platform 400 may comprise one or more processors 404 located on the same computing platform or not, which may be one or more Central Processing Units (CPU), microprocessors, electronic circuits, Integrated Circuits (IC) or the like. Processor 404 may be configured to provide the required functionality, for example by loading to memory and activating the software modules stored on a memory unit such as storage device 412 detailed below.

Computing platform 400 may comprise a communication device 408 for communicating with other devices or other computing platforms as necessary, for example obtaining information from the catheterization controller indicating locations and electrical measurements, storing data on remote storage devices, or the like. Communication module 408 may be adapted to interface with any communication channel such as Local Area Network (LAN), Wide Area Network (WAN), cellular network or the like, and use any relevant communication protocol.

Computing platform 400 may comprise a storage device 412, such as a hard disk drive, a Flash disk, a Random Access Memory (RAM), a memory chip, or the like. In some exemplary embodiments, storage device 412 may retain program code operative to cause processor 404 to perform acts associated with any of the modules listed below, or steps of the method of FIG. 3 above. The program code may comprise one or more executable units, such as functions, libraries, standalone programs or the like, adapted to execute instructions as detailed below.

Alternatively or additionally, the provided instructions may be stored on non-transitory tangible computer-readable media, such as magnetic, optical, or electronic memory.

Storage device 412 may comprise display and I/O module 416, for rendering a display to the user, to be displayed over display device 27, such as a map of the heart, plots of selected electrograms, or the like. Display and I/O module 416 may also be operative in receiving instructions and operation parameters from the user, for example highlighting locations assessed by any of the displayed electrograms, displaying a group of electrograms, or the like.

Storage device 412 may comprise communication module 420 for transmitting and receiving data to and from other parts of the system or other systems through communication device 408, such as catheter locations, associated electrograms, user preferences, histograms, or the like.

Storage device 412 may comprise unipolar disconnected electrodes discovery module 424 for calculating the correlation between a signal allegedly output by an electrode and a reference signal. Unipolar disconnected electrodes discovery module 424 may be further adapted to determine whether the correlation value is close beyond a predetermined threshold to −1, in which case the electrode may be identified as disconnected.

Storage device 412 may comprise bipolar disconnected electrodes discovery module 428 for calculating the correlation between two signals, each referring to two electrodes, including a common electrode associated with the two signals. Bipolar disconnected electrodes discovery module 428 may be further adapted to determine whether the correlation value is close beyond a predetermined threshold to −1, in which case the electrode common to the two signals may be identified as disconnected.

Storage device 412 may comprise electrical map generation module 432 for generating an electrical activity map of the heart, wherein the signals associated with disconnected electrodes are not taken into consideration when generating the map. If the number of disconnected electrodes or the percentage of disconnected electrodes out of the total number of electrodes exceeds a predetermined threshold, the map generation may be disabled due to insufficient relevant data.

Storage device 412 may comprise electrogram selection module 436 for selecting electrograms to be displayed, which may exclude electrograms associated with disconnected electrodes.

Storage device 412 may comprise additional action taking module(s) 440 for taking additional actions associated with disconnected electrodes, such as notifying a user.

It is appreciated that the steps and modules disclosed above are in addition to the software, hardware, firmware or other modules required for operating the catheter, displaying the catheterization process, performing other calculations such as signal analysis and in particular complex fractionated electrogram (CFE) analysis, generating the heart map, or the like. Further details for methods and systems may be found, for example in U.S. Pat. Nos. 8,676,305, 9,629,567, incorporated herein by reference in their entirety for any purpose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A method comprising: obtaining a plurality of electrical signals obtained from a plurality of electrodes distally disposed on a catheter inserted into one or more chambers of a heart of a patient, wherein at least one electrical signal obtained from at least one electrode of the plurality of electrodes obtains electrical activity in at least one location within the heart; identifying at least one signal from the plurality of electrical signals as being emitted from at least one disconnected electrode, said identifying utilizing a correlation with a reference signal measured within the heart, wherein the reference signal is associated with a reference electrode; and generating a map of electrical activity within the heart based upon the plurality of electrical signals, excluding at least one electrical signal originating from the at least one disconnected electrode.

Example 2

The method according to Example 1, wherein the plurality of electrical signals are Electrocardiography (ECG) signals.

Example 3

The method according to any of the previous examples, further comprising displaying to a user a representation of the plurality of electrical signals, excluding the at least one electrical signal originating from the at least one disconnected electrode.

Example 4

The method according to any of the previous examples, further comprising providing a notification to a user indicating the at least one disconnected electrode.

Example 5

The method according to any of the previous examples, wherein the at least one signal is identified by comparing the at least one signal to a reference signal.

Example 6

The method according to example 5, wherein said comparing comprises correlating between the at least one signal and the reference signal, and subject to said correlation providing a value that is within a predetermined distance from −1, further comprising indicating an electrode associated with the at least one signal as disconnected.

Example 7

The method according to any of the previous examples, wherein identifying the at least one signal comprises correlating a first signal and a second signal, the first signal measuring the potential difference between a first electrode and a second electrode, and the second signal measuring the potential difference between the second electrode and a third electrode.

Example 8

The method according to example 7, wherein said correlating is between the first signal and the second signal, and subject to said correlating providing a value that is within a predetermined distance from −1, identifying that the second electrode is disconnected and the at least one signal is associated with the second electrode.

Example 9

The method according to any of the previous examples, wherein the catheter comprises a basket-shape catheter tip.

Example 10

The method according to any of the previous examples, wherein the method is repeated every predetermined period of time as long as the catheter is within the heart, or according to a user's command, or according to a condition or protocol.

Example 11

The method according to example 10, wherein the method is omitted for electrodes that have been detected as disconnected.

Example 12

A computerized apparatus having a processor coupled with a memory unit, the processor being adapted to perform the steps of: obtaining a plurality of electrical signals obtained from a plurality of electrodes distally disposed on a catheter inserted into one or more chambers of a heart of a patient, wherein at least one electrical signal obtained from at least one electrode of the plurality of electrodes obtains electrical activity in at least one location within the heart; identifying at least one signal from the plurality of electrical signals as being emitted from at least one disconnected electrode, said identifying utilizing a correlation with a reference signal measured within the heart, wherein the reference signal is associated with a reference electrode; and generating a map of electrical activity within the heart based upon the plurality of electrical signals, excluding at least one electrical signal originating from the at least one disconnected electrode.

Example 13

The apparatus according to example 12, wherein the plurality of electrical signals are Electrocardiography (ECG) signals.

Example 14

The apparatus according to examples 12 or 13, wherein the processor is further adapted to display to a user a representation of the plurality of electrical signals, excluding the at least one electrical signal originating from the at least one disconnected electrode.

Example 15

The apparatus according to any of examples 12-14, wherein the processor is further adapted to provide a notification to a user indicating the at least one disconnected electrode.

Example 16

The apparatus according to any of examples 12-15, wherein the at least one signal is identified by correlating the at least one signal to a reference signal; and wherein subject to said correlation providing a value that is within a predetermined distance from −1, the processor is further adapted to indicate an electrode associated with the at least one signal as disconnected.

Example 17

The apparatus according to any of examples 12-16, wherein identifying the at least one signal comprises correlating a first signal and a second signal, the first signal measuring the potential difference between a first electrode and a second electrode, and the second signal measuring the potential difference between the second electrode and a third electrode, and wherein subject to said correlating providing a value that is within a predetermined distance from −1, the processor is further adapted to identify that the second electrode is disconnected and the at least one signal is associated with the second electrode.

Example 18

The apparatus according to any of examples 12-17, wherein the catheter comprises a basket-shape catheter tip.

Example 19

The apparatus according to any of examples 12-18, wherein the processor is adapted to repeat said steps every predetermined period of time as long as the catheter is within the heart, or according to a user's command, or according to a condition or protocol.

Example 20

A computer program product comprising a non-transitory computer readable medium retaining program instructions, which instructions when read by a processor, cause the processor to perform: obtaining a plurality of electrical signals obtained from a plurality of electrodes distally disposed on a catheter inserted into one or more chambers of a heart of a patient, wherein at least one electrical signal obtained from at least one electrode of the plurality of electrodes obtains electrical activity in at least one location within the heart; identifying at least one signal from the plurality of electrical signals as being emitted from at least one disconnected electrode, said identifying utilizing a correlation with a reference signal measured within the heart, wherein the reference signal is associated with a reference electrode; and generating a map of electrical activity within the heart based upon the plurality of electrical signals, excluding at least one electrical signal originating from the at least one disconnected electrode.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method of identifying a disconnected Intracardiac Electrogram (IEGM) electrode on a catheter while mapping electrical activity of a heart chamber of a patient, wherein the catheter includes a plurality of IEGM electrodes and a reference electrode, wherein the reference electrode is configured to be maintained within a blood pool of the heart chamber and the plurality of IEGM electrodes is configured to make contact with a wall of the heart chamber while the catheter is positioned within the heart chamber, the method comprising:

simultaneously sampling IEGM outputs from the plurality of IEGM electrodes and reference output from the reference electrode;

computing correlations between the IEGM outputs and the reference output;

determining correlation coefficients for the plurality of IEGM electrodes based on the computing;

identifying that a first IEGM electrode from the plurality of IEGM electrodes has a break in electrical connection within the catheter based on identifying a correlation coefficient of a correlation between output from the first IEGM electrode and the reference output is between −0.9 and −1; and updating a pool of the IEGM outputs applied to compute an electroanatomic map by removing the IEGM output from the first IEGM electrode from the pool of the IEGM outputs; and computing a map of electrical activity within the heart chamber based on the updated pool of the IEGM outputs; and rending the map on a display.

2. The method of claim 1, further comprising displaying on the display a notification to a user indicating that the first IEGM electrode is disconnected.

3. The method of claim 1, wherein the IEGM outputs are defined between bipolar pairs of the IEGM electrodes and wherein the correlations computed are between the IEGM outputs from bipolar pairs of the IEGM electrodes and the reference output.

4. The method of claim 3, wherein the first IEGM electrode is identified based on comparing correlations from two different bipolar pairs, each including the first IEGM electrode.

5. The method of claim 3, wherein the first IEGM electrode is identified based on correlation from a bipolar pair defined by output from a second IEGM electrode subtracted from the output from the first IEGM electrode.

6. The method of claim 1, wherein the method is repeated every predetermined period of time as long as the catheter is within the heart chamber.

7. A computerized apparatus configured for identifying a disconnected IEGM electrode on a catheter that is mapping electrical activity of a heart chamber of a patient, wherein the catheter includes a plurality of Intracardiac Electrogram (IEGM) electrodes and a reference electrode, wherein the reference electrode is configured to be maintained within a blood pool of the heart chamber and the plurality of IEGM electrodes is configured to make contact with a wall of the heart chamber while the catheter is positioned within the heart chamber, the apparatus comprising:

a processor coupled with a memory unit, the processor being adapted to perform the steps of:

receiving IEGM outputs from the plurality of IEGM electrodes and reference output from the reference electrode, wherein the IEGM outputs and the reference output are simultaneously sampled;

computing correlations between the IEGM outputs and the reference output;

determining correlation coefficients for the plurality of IEGM electrodes based on the computing;

identifying that a first IEGM electrode from the plurality of IEGM electrodes has a break in electrical connection within the catheter based on identifying a correlation coefficient of a correlation between an IEGM output from the first IEGM electrode and the reference output is between −0.9 and −1; and updating a pool of the IEGM outputs applied to compute an electroanatomic map by removing the IEGM output from the first IEGM electrode from the pool of the IEGM outputs; and computing a map of electrical activity within the heart chamber based on the updated pool of the IEGM outputs; and rendering the map on a display.

8. The apparatus of claim 7, wherein the processor is configured to provide a notification to a user on a display indicating the first IEGM electrode.

9. The apparatus of claim 7, wherein the IEGM outputs are defined between bipolar pairs of the IEGM electrodes and wherein the correlations computed are between the IEGM outputs from bipolar pairs of the IEGM electrodes and the reference output.

10. The apparatus of claim 9, wherein the first IEGM electrode is identified based on comparing correlations from two different bipolar pairs that include the first IEGM electrode.

11. The apparatus of claim 9, wherein the first IEGM electrode is identified based on correlation from a bipolar pair defined by output from a second IEGM electrode subtracted from the output from the first IEGM electrode.

* * * * *